United States Patent [19]

DePompei et al.

[11] 4,281,125
[45] Jul. 28, 1981

[54] QUINOLINE CATALYZED SYNTHESIS OF PYRIDAZINONE PHARMACEUTICAL INTERMEDIATES

[75] Inventors: Michael F. DePompei; Alex Hlynsky, both of Mentor, Ohio

[73] Assignee: Diamond Shamrock Corporation, Dallas, Tex.

[21] Appl. No.: 149,918

[22] Filed: May 15, 1980

[51] Int. Cl.³ ................. C07D 237/14; C07D 237/24; C07D 237/22; C07D 237/18
[52] U.S. Cl. .................................... 544/239; 544/224; 544/240; 560/35
[58] Field of Search ............................... 544/239, 240

[56] References Cited

U.S. PATENT DOCUMENTS

| | | | |
|---|---|---|---|
| 2,839,532 | 6/1958 | Drney et al. | 544/239 |
| 3,491,096 | 1/1970 | Baetz | 544/240 |
| 3,657,242 | 4/1972 | Houlihan | 544/224 |
| 3,689,652 | 9/1972 | Curran | 424/250 |
| 3,746,712 | 7/1973 | Ross | 544/239 |
| 3,812,256 | 5/1974 | Curran | 424/250 |
| 3,822,260 | 7/1974 | Curran | 344/239 |
| 3,876,786 | 4/1975 | McEvoy | 424/250 |
| 3,876,787 | 4/1975 | McEvoy | 424/250 |
| 3,931,177 | 1/1976 | Coates | 544/239 |
| 3,975,388 | 8/1976 | Hakim | 544/239 |

FOREIGN PATENT DOCUMENTS 840522 7/1960 United Kingdom ..................... 544/239

*Primary Examiner*—Mark L. Berch
*Attorney, Agent, or Firm*—Stuart L. Melton; Walter C. Danison, Jr.

[57] ABSTRACT

Valuable pyridazinone intermediates to pharmaceutically useful compounds can be prepared in surprisingly high yields by the quinoline catalyzed reaction of the corresponding monohydrazone with an appropriately substituted acetic acid ester. In an especially preferred embodiment, p,p'-dichlorobenzil monohydrazone and methyl acetoacetate are reacted in a xylene solvent in the presence of quinoline to afford 4-acetyl-5,6-bis(p-chlorophenyl)-2H-pyridazin-3-one, which can then be reacted with ethylene carbonate in the presence of potassium carbonate to afford the antihypertensive agent, 4-acetyl-5,6-bis(p-chlorophenyl)-2-(2'-hydroxyethyl)-2H-pyridazin-3-one.

24 Claims, No Drawings

QUINOLINE CATALYZED SYNTHESIS OF PYRIDAZINONE PHARMACEUTICAL INTERMEDIATES

TECHNICAL FIELD OF THE INVENTION

The present invention provides an improved process for the synthesis of pyridazinones which are valuable intermediates to pharmaceutically useful compounds, said process comprising the quinoline catalyzed reaction of the corresponding monohydrazone with an appropriately substituted acetic acid ester.

BACKGROUND OF THE PRIOR ART

Substituted pyridazinone compounds having various substituents have heretofore been prepared and proposed for use in a wide range of different ultimate applications. Thus, for example, U.S. Pat. Nos. 3,657,242; 3,689,652; 3,746,712; 3,812,256; 3,822,260; 3,876,786; 3,876,787; 3,931,177; and 3,975,388 disclose a variety of pharmacologically active 4,5-dihydropyridazinones. As a chemical class, those compounds comprise dihydro (saturated) ketopyridazines.

Representative of another class of related compounds are the pyridaz-3-one compounds disclosed in U.S. Pat. No. 2,839,532. The aforesaid patent is directed to 4,5-unsaturated pyridaz-3-one (or 3-ketopyridazine) compounds having a cyano, acetyl, carboxyl, carbethoxy or benzoyl group in the 4-position optionally substituted in the 5,6- positions by lower alkyl, phenyl or substituted phenyl residues. These compounds are disclosed as being useful as medicaments, particularly, analgesics, anesthetics, antibacterials or disinfectants.

U.S. Pat. No. 3,491,096 and British Pat. No. 840,522 are directed to other previously investigated pyridazone compounds. The aforementioned British patent pertains to 2-hydroxymethyl-6-phenyl-3-pyridazone and the analgesic utility thereof. U.S. Pat. No. 3,491,096 describes 2-pyridylalkylated-6-phenylpyridaz-3-one compounds possessing sedative, analgesic and antispasmodic properties, with occasional hypotensive effects being observed.

Copending Powers et al U.S. Patent Application Ser. No. 11,416, filed Feb. 12, 1979, now U.S. Pat. No. 4,238,490 and assigned to the assignee hereof, describes novel pyridazin(2H)-3-ones of the general formula

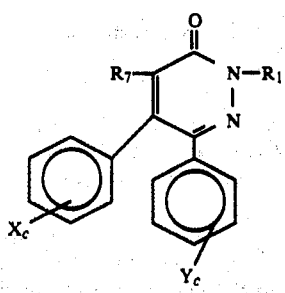

(I)

and pharmaceutically acceptable nontoxic salts thereof wherein $R_1$ is hydrogen, $C_1$–$C_4$ hydroxyalkyl, $C_1$–$C_4$ carbamylmethyl, $C_1$–$C_6$ carboxyalkyl, $C_1$–$C_6$ alkoxycarbonyl($C_1$–$C_6$)alkyl, $C_1$–$C_6$ alkoxy($C_1$–$C_6$)alkyl; or the group

where a is 1 to 4, inclusive, $R_2$ is hydrogen or $C_1$–$C_4$ alkyl and $R_3$ is amino, methylthio, $C_1$–$C_6$ alkylamino, $C_1$–$C_6$ alkylimino, $C_1$–$C_6$ acylamino, $C_1$–$C_6$ alkoxycarbonylamino, morpholinyl, piperazinyl, ($C_1$–$C_6$ alkoxycarbonyl)piperazinyl, piperidinyl, pyrrolidinyl, glucuronyl or glucopyranosyl; or the group

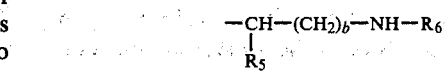

where $R_4$ is hydrogen, $C_1$–$C_{20}$ alkyl, $C_1$–$C_6$ carboxyalkyl, phenyl, phenyl($C_1$–$C_6$)alkyl, or $R_4$ represents the group

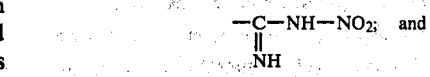

where b is 0 to 4, inclusive, $R_5$ is hydrogen, $C_1$–$C_4$ alkyl, methylthioethyl, benzyl, $NH_2$, or benzyloxycarbamyl, and $R_6$ is hydrogen, benzyloxycarbonyl, t-butyloxycarbonyl or $$-\underset{\underset{NH}{\|}}{C}-NH-NO_2;\ and$$

$R_7$ is acetyl, cyano, phenylsulfonyl, ($C_1$–$C_4$)alkylhydrazono, naphthyl, phenyl or phenyl substituted with at least one substituent selected from the group consisting of halogen, $C_1$–$C_6$ alkylamino and $C_1$–$C_4$ alkoxy; and $X_c$ and $Y_c$ are the same or different and are independently selected from the group consisting of halogen, $C_1$–$C_4$ alkyl and $C_1$–$C_4$ alkoxy where c is 0, 1 or 2; subject to the provisos that when $R_7$ is acetyl, phenyl or cyano, $R_1$ is other than hydrogen; and when $R_7$ is cyano, $R_1$ is $C_1$–$C_4$ hydroxyalkyl, $C_1$–$C_6$ carboxyalkyl or the group

where $R_4$ is $C_1$–$C_6$ carboxyalkyl and $X_c$ and $Y_c$ are halo, with c being at least 1;

and the enol tautomeric derivatives and metabolites thereof. Said compounds are useful therapeutic antihypertensive agents, as described in the aforesaid U.S. Application Ser. No. 11,416, now U.S. Pat. No. 4,238,490 said application being hereby incorporated by reference in its entirety and relied upon.

As used throughout the instant specification and claims, the expressions "alkyl" and "alkoxy" are inclusive of straight and branched chain carbon-carbon linkages, e.g., methyl, ethyl, n-propyl, isopropyl, n-butyl, isobutyl, sec-butyl, tert-butyl, isohexyl, etc. The expression "acyl" includes, e.g., formyl, acetyl, propionyl, butanoyl, pentanoyl, hexanoyl and the like. The term "halo" includes chlorine, fluorine, bromine and iodine. The expression "pharmaceutically acceptable nontoxic salts," as used herein, is intended to include those salts capable of being formed with the compounds of formula (I) without materially altering the chemical structure or pharmacological properties of the parent compounds. Representative of acids for reaction with sufficiently basic pyridazinone derivatives include hydrochloric, hydrobromic, hydroiodic, nitric, phosphoric, citric, etc. Alkali metal salts of carboxylic acid derivatives of formula (I) may be obtained by reaction with suitable bases, e.g., sodium hydroxide, potassium hydroxide, etc. Alkaline earth metal salts may be similarly obtained. Additionally, compounds of formula (I) containing amino acid residues, i.e., an α-amino acyl group, may be obtained as their hydrate salts such as mono- or di-hydrobromide, hydrochloride, etc., hydrate and such inorganic and organic acid addition salts of certain of the compounds of formula (I) and amino acid residues or derivatives may advantageously be employed to, for instance, alter solubility properties or augment bioavailability.

As will be apparent to those skilled in the art, the keto compounds of formula (I) wherein $R_1$ is hydrogen may be present in the enol tautomeric form. It is also noted that certain of the $R_1$ substituents at the 2-position, e.g., hydroxyalkyl, carboxyalkyl, alkoxycarbonylalkyl, alkoxyalkyl, alkylaminoalkyl, glucuronyl, etc., constitute possible enolic derivatives and/or metabolites of compounds within the scope of the present invention.

U.S. Application Ser. No. 11,416 now U.S. Pat. No. 4,238,490 teaches that the subject pyridazinones, i.e., substituted keto-pyridazine compounds of formula (I), may be prepared by various alternative methods theretofore employed in the synthesis of other pyridazinone compounds (e.g., in U.S. Pat. No. 2,839,532) or modifications thereof to obtain the $R_1$, $R_7$, $X_c$ or $Y_c$ substituents thereon as defined above. In general, one method for the preparation of pyridazin(2H)-3-ones comprises reacting an appropriately substituted monohydrazone, with the appropriately substituted acetic acid ester or reacting the appropriately substituted benzil and appropriately substituted hydrazide under cyclization conditions, e.g., in the presence of suitable solvents, such as xylene, acetonitrile, methanol, benzene, etc., and alkaline condensing agents, such as hydroxides, alcoholates, hydrides, alkali or alkaline earth metals, tertiary amines, etc., to effect ring closure. The foregoing general reaction scheme may be depicted as follows

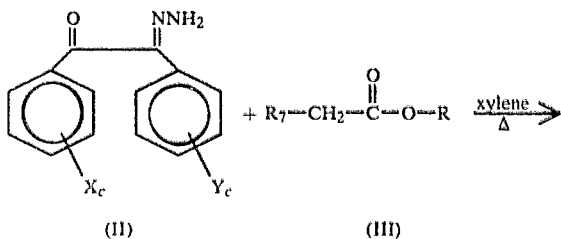

(II)    (III)

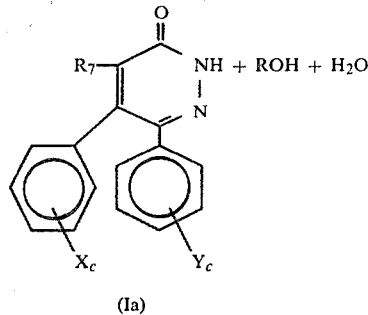

(Ia)

wherein R is typically an alkyl group and $R_7$ is not here restricted by the provisos set forth earlier. As will be apparent from the foregoing description of the formula (I) substituents, the formula (Ia) products are in some instances pharmacologically active compounds of formula (I), while in other instances the formula (Ia) products are intermediates which can be converted by subsequent reactions to the compounds of formula (I).

The monohydrazone reactants may be prepared by the reaction of an appropriate substituted benzil with hydrazine hydrate. Suitable benzil starting materials may be obtained commercially or prepared by known methods, for example, cyanide ion catalyzed benzoin condensation followed by oxidation. The pyridazin(2H)-3-one compounds thus prepared may be utilized following suitable recrystallization/purification as intermediates for the preparation of further 2-substituted derivatives in accordance with the above $R_1$ definition.

Exemplary of preferred compounds for use in the antihypertensive compositions and methods of U.S. Ser. No. 11,416 now U.S. Pat. No. 4,238,490 are compounds of the above general formula (I) wherein, correspondingly, $R_1$ represents $C_1$-$C_4$ hydroxyalkyl (especially, hydroxyethyl), esters thereof, e.g., acetate, butyrate, propanoate, formate, hemisuccinate, octadecanoate, benzoate, etc.; amino acid esters thereof corresponding to the

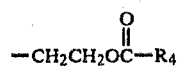

group defined hereinabove wherein $R_4$ represents

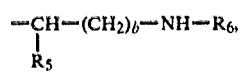

e.g., lysine, glycine, methionine, phenylalanine, etc.; or where $R_1$ is $C_1$-$C_4$ carbamylmethyl, e.g., α-acetamido; aminoalkyl, e.g., aminomethyl, aminoethyl, etc.; $C_1$-$C_6$ alkylaminoethyl, e.g., dimethylaminoethyl; glucopyranosyl; glucuronyl; 1-morpholinylethyl; 1-piperidinylethyl; 1-pyrrolidinylethyl and acetamidoethyl; and wherein $R_7$ represents acetyl and $X_c$ and $Y_c$ are para-halo, preferably para-chloro. An especially preferred antihypertensive agent provided by U.S. Ser. No. 11,416 is 4-acetyl-5,6-bis(p-chlorophenyl)-2-(2′-hydroxyethyl)-2H-pyridazin-3-one. According to the methods described in Ser. No. 11,416, that compound is prepared by first reacting ethanol and sodium to form sodium ethoxide, then adding ethyl acetoacetate and p,p'-dichlorobenzil monohydrazone, to afford 4-acetyl-5,6-bis(p-chlorophenyl)-2H-pyridazin-3-one in 20% yield. That intermediate is then reacted with ethylene carbonate and potassium hydroxide in dimethylformamide to afford the desired final product. The intermediate 4-acetyl-5,6-bis(p-chlorophenyl)-2H-pyridazin-3-one can be used to prepare other antihypertensive compounds of Ser. No. 11,416 as well. See, for example, Examples 9, 10 and 11 therein. However, the poor yields heretofore obtained in the preparation of that key intermediate have been a serious problem standing in the way of commercialization of the final antihypertensive products such as 4-acetyl-5,6-bis(p-chlorophenyl)-2-(2'-hydroxyethyl)-2H-pyridazin-3-one.

In view of the foregoing, it is apparent that a serious need exists for an improved process for the preparation of the antihypertensive agents of formula (I) and intermediates thereto.

SUMMARY OF THE INVENTION

It is therefore a primary object of the present invention to provide an improved process for the preparation of the antihypertensive agents of formula (I) and intermediates thereto. More particularly, it is a primary object of the present invention to provide an improved process for the preparation of compounds of formula (Ia) in substantially higher yields than heretofore possible, thus affording a commercially viable route to the formula (I) antihypertensives.

These and similar objects are accomplished according to the present invention by the quinoline catalyzed reaction of a monohydrazone of formula (II) above with an appropriately substituted acetic acid ester of formula (III) above in a suitable solvent, at elevated temperature, to afford the corresponding compound of formula (Ia).

DETAILED DESCRIPTION OF THE PREFERRED EMBODIMENTS

Preferred monohydrazones of formula (II) for use in the instant process are those wherein $X_c$ and $Y_c$ are para-halo, a particularly preferred monohydrazone starting material being p,p'-dichlorobenzil monohydrazone. In formula (III), $R_7$ is preferably acetyl and R is preferably lower alkyl. Accordingly, preferred starting materials of formula (III) are ethyl acetoacetate and methyl acetoacetate, with the latter being especially preferred. The solvent of choice is xylene, particularly when p,p'-dichlorobenzil monohydrazone and methyl acetoacetate are employed as the reactants. However, other suitable organic solvents will be apparent to those skilled in the art.

It has surprisingly been found that quinoline is vastly superior to the sodium alkoxide condensing agents typically used in the prior art. Also, quinoline has been found to be a much more effective catalyst than pyridine. Thus, only 20% yields of 4-acetyl-5,6-bis(p-chlorophenyl)-2H-pyridazin-3-one are reported in U.S. Ser. No. 11,416 when using a sodium ethoxide reagent to effect ring closure. Similarly, it has more recently been found that use of pyridine as the condensing agent affords the desired 4-acetyl-5,6-bis(p-chlorophenyl)-2H-pyridazin-3-one in less than 35% yield. In contrast, yields of up to 76% of the aforesaid key intermediate have been obtained when using quinoline to catalyze the reaction. It has also surprisingly been found that, with quinoline, yields of up to 76% are obtained using only half as much catalyst as required in the case of pyridine. In fact, a ratio of 1 g quinoline per 7.1 g monohydrazone (1.0 mole quinoline/3.16 moles monohydrazone) has afforded yields comparable to those obtained with 1 g quinoline/3.5 g monohydrazone, and considerably superior to those obtained with 1 g pyridine/3.4 g monohydrazone.

The process of the present invention is most advantageously conducted under carefully controlled reaction conditions, especially as concerns time and temperature. Obviously, precise time and temperature ranges will vary with the particular reactants employed. In the preferred embodiment of the instant process, wherein methyl acetoacetate and p,p'-dichlorobenzil monohydrazone are reacted in the presence of quinoline in a xylene solvent to afford the desired 4-acetyl-5,6-bis(p-chlorophenyl)-2H-pyridazin-3-one, the xylene is heated to about 120° C. before the monohydrazone is added; the monohydrazone-xylene mixture is heated rapidly to about 125°–130° C.; and the methyl acetoacetate and quinoline are then added as rapidly as possible, while maintaining the temperature at about 125°–130° C. The total reaction time is generally of the order of 2.5 to 3.0 hours. Stripping of the solvent is not necessary prior to isolation of the product.

The condensation of a methyl acetoacetate molecule with p,p'-dichlorobenzil monohydrazone may go in either of two directions, as depicted below.

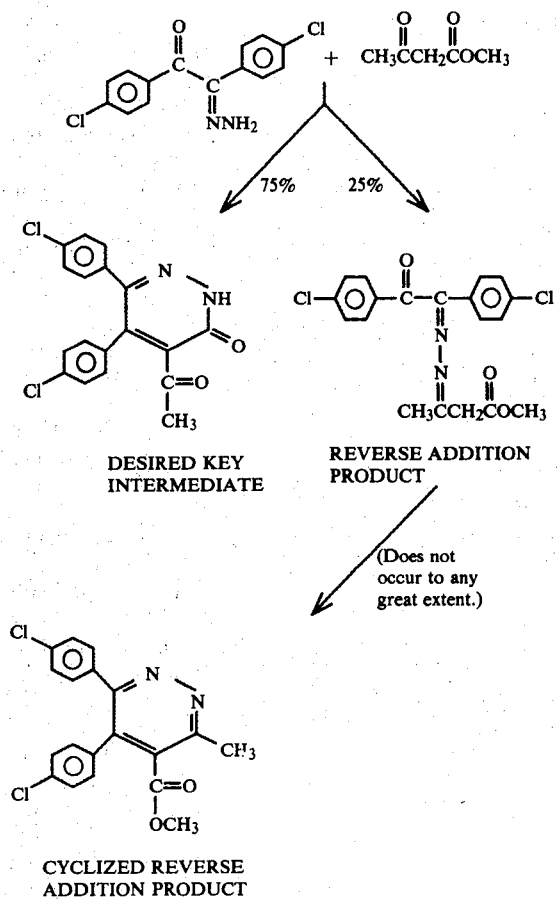

DESIRED KEY INTERMEDIATE

REVERSE ADDITION PRODUCT (Does not occur to any great extent.)

CYCLIZED REVERSE ADDITION PRODUCT

The formation of the desired pyridazinone key intermediate is favored at temperatures above 110° C. The undesired reverse addition product, 3-(4,4'-dichlorobenzilmonoazino)-1-methoxy-1,3-butanedione, is favored at lower temperatures and may even constitute the major reaction product under improper reaction conditions. It is also important that the methanol (and water) by-products be removed from the reaction zone as they are formed. Because the monohydrazone degrades at elevated temperatures, the initial reaction with elimination of the methanol by-product should be carried out rapidly. Presence of p-chlorobenzoic acid, hydrazine or methanol in the monohydrazone feedstock reduces yields. Therefore, the monohydrazone starting material should be of high quality. To obtain the desired degree of purity, the monohydrazone starting material [which has typically been prepared by (1) a classical benzoin condensation in which p-chlorobenzaldehyde in the presence of potassium cyanide is converted to p,p'-dichlorobenzoin in refluxing methanol and water solvents; followed by (2) oxidation of the dichlorobenzoin to the dichlorobenzil using concentrated nitric acid in glacial acetic acid solvent; followed by (3) conversion of the dichlorobenzil to the monohydrazone by reaction with hydrazine hydrate in isopropanol at reflux temperature] is recrystallyzed from isopropanol prior to its use in the cyclization process of the present invention.

In a particularly preferred embodiment of the present invention which provides 4-acetyl-5,6-bis(p-chlorophenyl)-2H-pyridazin-3-one, the following procedure has been utilized:

The reactor is preheated by refluxing xylene (about 140° C.). Sufficient xylene is distilled and removed to ensure that any moisture present in the reactor and in the xylene has been eliminated. The xylene is then cooled to about 130° C., and solid p,p'-dichlorobenzil monohydrazone is added. The mixture is quickly heated, then methyl acetoacetate and quinoline are added. Immediately thereafter, a methanol-xylene emulsion distilling at about 138° C. (pot temperature) is removed. (The time which elapses from the beginning of the monohydrazone addition through the heat-up stage, the methyl acetoacetate and quinoline addition to the beginning of the methanol distillation is generally less than 10 minutes.) The mixture is held at reflux temperature for about 2 hours, during which time approximately 90% of the theoretical amount of methanol and water are removed by distillation. During the methanol-water distillation and very early in the run, a light brown precipitate, which is the desired 4-acetyl-5,6-bis(p-chlorophenyl)-2H-pyridazin-3-one, begins to form in the hot xylene solution.

The reverse addition product precipitates as a flocculent material and is much more soluble, generally dropping out of solution when the temperature goes below 40° C. If the content of desired product is in excess of about 65%, then the xylene solution can be cooled to about 20° C. without crystallizing out the reverse addition product. On the other hand, if the content of desired product is less than about 55%, the filter collection of product should be done at about 40° C. Otherwise, when the temperature drops below 40° C., a precipitate which is a mixture of desired compound and the reverse addition product is obtained.

After the methanol-water has been removed, approximately half of the reaction xylene is then removed by distillation over an approximately one hour period. The mixture is then generally cooled to room temperature and the crystallized 4-acetyl-5,6-bis(p-chlorophenyl)-2H-pyridazin-3-one is removed by filtration, washed with methanol and dried. Following this procedure, yields of about 75% can be expected, with the product being more than 98% pure 4-acetyl-5,6-bis(p-chlorophenyl)-2H-pyridazin-3-one.

It has been observed that the desired 4-acetyl-5,6-bis(p-chlorophenyl)-2H-pyridazin-3-one has low solubility in xylene. The uncyclized reverse addition product has high solubility in xylene. However, it is very important that very little of the uncyclized reverse addition product become cyclized because the solubility characteristics of the desired pyridazin-3-one and of the cyclized reverse addition product are very similar. Consequently, the heating time after the water and methanol have been removed should be limited to minimize dehydration of the reverse addition product to its cyclized version.

Because 4-acetyl-5,6-bis(p-chlorophenyl)-2H-pyridazin-3-one is the immediate precursor to the desired antihypertensive agent 4-acetyl-5,6-bis(p-chlorophenyl)-2-(2'-hydroxyethyl)-2H-pyridazin-3-one, a high degree of purity of the precursor is required. Therefore, the crystalline product obtained by the instant process as described above is recrystallized from ethyl acetate. The recrystallization comprises dissolving the 4-acetyl-5,6-bis(p-chlorophenyl)-2H-pyridazin-3-one in hot ethyl acetate, filtering, removing a portion of the solvent by distillation and collecting the desired 4-acetyl-5,6-bis(p-chlorophenyl)-2H-pyridazin-3-one by filtration at about 20° C.

The preferred product of the instant process, i.e., 4-acetyl-5,6-bis(p-chlorophenyl)-2H-pyridazin-3-one, after purification as described supra, can then be converted to the antihypertensive agent 4-acetyl-5,6-bis(p-chlorophenyl)-2-(2'-hydroxyethyl)-2H-pyridazin-3-one, preferably by reaction with ethylene carbonate in dimethylformamide solvent in the presence of trace quantities of potassium carbonate at about 85° C., followed by crystallization from ethyl acetate.

Without further elaboration, it is believed that one of ordinary skill in the art can, using the preceding description, utilize the present invention to its fullest extent. Consequently, the preferred specific embodiments set forth below are to be construed as merely illustrative and not limitative of the remainder of the specification and claims in any way whatsoever.

In the Examples which follow, it is to be noted that Examples 1–3 are illustrative of starting material preparations; Examples 4 and 5 are comparative examples of the procedures used and yields obtained previously; Examples 6–9 are illustrative of the improved process of the present invention; and Example 10 is illustrative of methods for converting a product of the instant process into an antihypertensive agent of formula (I).

EXAMPLE 1

A 20 gallon (approximately 76.9 liter) reaction vessel was charged with 22.7 kg of p-chlorobenzaldehyde and the solids were blanketed with nitrogen. 12.6 Liters of methanol were added, and the resultant mixture was agitated and heated. When the temperature reached 50° C., the solids had dissolved and 6.0 liters of distilled water were added. Heating was continued until the temperature reached 79° C., at which time 544 g of potassium cyanide dissolved in 1.3 liters of water were added. The methanol began refluxing vigorously and the solution turned a bright orange color. The exothermic reaction was essentially complete within 30 minutes, but heating was continued at methanol reflux temperature for an additional hour.

The reaction product was cooled to 50° C., 20 liters of cold water were added, and the mixture was agitated. Then the orange colored organic layer was allowed to settle and the water-methanol upper layer was removed under nitrogen. The organic layer was washed twice more with 8 liter portions of water, the final wash being carried out at 60° C. to prevent solidification of the organic layer. There was thus obtained the desired p,p'-dichlorobenzoin.

EXAMPLE 2

To the washed p,p'-dichlorobenzoin obtained in Example 1 were added 21.3 liters of glacial acetic acid. The mixture was agitated and heated to 97° C., then 13.7 kg of concentrated nitric acid were added over a one hour period. The reaction mixture was heated at 97°-100° C. for an additional six hours, an additional six liters of glacial acetic acid being added during the oxidation period to maintain fluidity of the thickening slurry.

After the oxidation was completed, the reaction mixture was cooled to 25° C. and transferred to a filter crock. The bright yellow-colored product was thoroughly washed with water. The washed product was divided into four portions, and each portion was returned to the reaction vessel and stirred with 10 gallons (approximately 38.5 liters) of an approximately 5% bicarbonate solution to neutralize any residual acids and to remove p-chlorobenzoic acid by-product.

The bicarbonate washed p,p'-dichlorobenzil was returned to the crock filter, washed thoroughly with water and dried overnight at 120° C. The weight of dried p,p'-dichlorobenzil was 17.5 kg, a 77% yield based on the amount of p-chlorobenzaldehyde charged in Example 1.

EXAMPLE 3

A 20 gallon (76.9 liter) reaction vessel was charged with 5.0 kg of p,p'-dichlorobenzil and 37 liters of isopropyl alcohol. The mixture was agitated and heated to 85° C., then 1.03 kg of 85% hydrazine hydrate were added. Within twenty minutes, the slurry became a clear solution. An additional 200 g of hydrazine hydrate were then added. Within 30 minutes after the second hydrazine addition, the desired p,p'-dichlorobenzil monohydrazone began to precipitate and to form a thick slurry. The slurry was stirred for one additional hour at 85°-90° C., then was cooled to 25° C. The monohydrazone was transferred to a filter crock and washed with isopropyl alcohol. The washed monohydrazone was returned to the reaction vessel, 25 liters of isopropyl alcohol were added and the mixture was heated to 80° C. with agitation. The reaction mixture was then cooled to 25° C., transferred to the filter crock, washed with isopropyl alcohol and dried overnight at 65° C. The total weight of dry p,p'-dichlorobenzil monohydrazone was 14.86 kg, an 81% yield based on the p,p'-dichlorobenzil.

EXAMPLE 4

Ethanol, dried by distilling from Mg-$I_2$, was added to a dry flask ($N_2$ atmosphere) containing clean sodium (1.1 equivalent). After the sodium had reacted, ethyl acetoacetate (7 ml) was added dropwise to the cold (0°-5° C.) alkoxide solution. p,p'-Dichlorobenzil monohydrazone (15 g) was added through a powder addition funnel. After heating the reaction mixture at reflux for three hours, it was cooled and poured into 1 N HCl. The resulting precipitate was separated by filtration and washed with water. The resulting product was recrystallized from ethanol-acetonitrile to give 4-acetyl-5,6-bis(p-chlorophenyl)-2H-pyridazin-3-one melting at 269°-271° C., in 20% yield.

Analysis—calculated for $C_{18}H_{12}Cl_2N_2O_2$(%): C, 60.20; H, 3.34; N, 7.80. Found (%): C, 60.02; H, 3.33; N, 7.91.

EXAMPLE 5

A 20 gallon (76.9 liter) reaction vessel was charged with 34.2 liters of xylene and 13.76 kg of p,p'-dichlorobenzil monohydrazone. The mixture was heated up to 60° C. over a 20 minute period and 4.125 liters of pyridine were then added. Heating was continued for an additional 30 minutes, during which time the reaction temperature climbed to 110° C. 6.0 Kg of methyl acetoacetate diluted with 5.5 liters of xylene were then added. Water began to distill immediately. Over the next 5 hours, 1.25 liters of water were removed by azeotropic distillation. The temperature was then raised and 28.5 liters of pyridine and xylene were removed by distillation.

The reaction mixture was cooled to 40° C. and the solids were collected by filtration and washed, first with xylene and then with petroleum ether. The crude product was dried at 75° C. for 6 hours. There were thus obtained 5.845 kg of crude 4-acetyl-5,6-bis(p-chlorophenyl)-2H-pyridazin-3-one melting at 262°-270° C. (34.7% yield based on monohydrazone charged). The crude product was slurried in methanol to remove a red-brown colored solid which was soluble in the methanol. Total reaction time to convert the monohydrazone to the pyridazin-3-one was 10 hours, with an additional one hour for methanol wash and an additional 12 hours for drying time.

EXAMPLE 6

A flask fitted with a stirrer, Deans Stark trap, condenser, thermometer and addition funnel, was charged with xylene and p,p'-dichlorobenzil monohydrazone. The mixture was heated with stirring to 105° C. and then charged with methyl acetoacetate, followed immediately with quinoline. The mixture was refluxed for approximately two and one-half hours, then cooled to 45°-50° C., filtered, washed with methanol, dried and weighed. The product was 4-acetyl-5,6-bis(p-chlorophenyl)-2H-pyridazin-3-one. The particulars for several runs are shown in the following table.

TABLE I

| | Quantities of Starting Materials | | | | | | |
|---|---|---|---|---|---|---|---|
| Run Number | Monohydrazone | Methyl Acetoacetate | Quinoline | Xylene | Weight of Product | Yield | Melting Point |
| 1 | 25.0 g | 14 ml | 7 ml | 60 ml | 22.5 g | 70% | 268-270° C. |
| 2 | 25.0 g | 14 ml | 3.5 ml | 60 ml | 22.7 g | 74% | 268-270° C. |
| 3 | 100.0 g | 48 ml | 14 ml | 240 ml | 89.0 g | 72.6% | 268-270° C. |
| 4 | 200.0 g | 96 ml | 28 ml | 480 ml | 167 g | 68.4% | 269-270° C. |

TABLE I-continued

| | Quantities of Starting Materials | | | Weight | | |
|---|---|---|---|---|---|---|
| Run Number | Monohydrazone | Methyl Acetoacetate | Quinoline | Xylene | of Product | Yield | Melting Point |
| 5* | 876 g | 416 ml | 122 ml | 3725 ml | 813 g | 75.7% | Not recorded |

*In this run, xylene solvent was heated to 110° C., then the monohydrazone was added. That mixture was heated to 124-125° C., then methyl acetoacetate, followed by quinoline, was added.

EXAMPLE 7

A 5 liter flask fitted with a stirrer, Deans Stark trap, water cooled condenser, thermometer, and addition funnel was charged with 1200 ml of xylene. The xylene was heated to 120° C. Then, 500 g of p,p'-dichlorobenzil monohydrazone were added and the resultant mixture was heated to 126° C. 240 Ml of methyl acetoacetate and 70 ml of quinoline were added in sequence at such a rate as to maintain the reaction temperature between 126° and 128° C. (approximately 8 minute addition time). The reaction mixture was then refluxed for approximately two and one-half hours at 137° C. At the end of that time, the flask was cooled to 45° C., and the solids were removed by filtration, washed with methanol, and dried. A yield of 348 g (57% yield) of the desired 4-acetyl-5,6-bis(p-chlorophenyl)-2H-pyridazin-3-one, melting at 269°-271° C., was obtained.

EXAMPLE 8

A 20 gallon (76.9 liter) reaction vessel was preheated by refluxing xylene (140° C.). Sufficient xylene was distilled and removed to ensure that moisture in the reactor and in the xylene was eliminated. The xylene was cooled to 130° C. by shutting off the steam to the reactor and solid monohydrazone was added. The resultant mixture was quickly heated, then methyl acetoacetate and quinoline were added through a liquid feed tube. Immediately thereafter, a methanol-xylene emulsion distilling at 138° C. was removed. The time which elasped from the beginning of the monohydrazone addition, through the heat-up stage and the methyl acetoacetate and quinoline addition, to the beginning of the methanol distillation was less than 10 minutes.

The mixture was held at the reflux temperature for about two hours, during which time approximately 90% of the theoretical amount of methanol and water were removed by distillation. Approximately half of the reaction xylene was then removed by distillation (time elapsed, approximately one hour). The reaction mixture was then cooled to room temperature and the crystalline 4-acetyl-5,6-bis(p-chlorophenyl)-2H-pyridazin-3-one which formed was collected by filtration. The crystals were washed with methanol until the methanol filtrate was clear. The product was greater than 98% pure. The particulars for two runs are given in the following table.

TABLE II

| | Quantities of Starting Materials | | | | | |
|---|---|---|---|---|---|---|
| Run Number | Mono-hydrazone | Methyl Aceto-acetate | Quino-line | Xy-lene | Weight Of Product | Yield |
| A | 3680 g | 1766 ml | 515 ml | 17 l | 3480 g | 75.6% |
| B | 5550 g | 2644 ml | 777 ml | 24 l | 5129 g | 75.4% |

EXAMPLE 9

A 12 liter flask immersed in a heating mantle was charged with 6 l of xylene and heated to 100° C. Then, 1409 g (4.81 mole) of p,p'-dichlorobenzil monohydrazone (m.p. 159°-160° C.) was rapidly added. A reaction flask head containing a stirrer was quickly attached to the flask and equipped with a dropping funnel and a Barrett type water trap with a condenser. The mixture was heated with rapid stirring and, when the pot temperature reached 120° C., 675 ml (6.26 mole) of methyl acetoacetate (b.p. 169°-170° C., density=1.076) were added quickly from the dropping funnel, followed immediately by 197 ml of quinoline. Almost immediately following the quinoline addition, a methanol-xylene emulsion began to distill (at 128° C.) into the Barrett water trap. Total time elapsed between the monohydrazone addition and the methanol-xylene azeotrope distillation was 10 minutes.

The temperature rose to 136°-139° C. and the methanol-xylene azeotrope, followed by the water-xylene azeotrope, distilled. The methanol-water lower layer was removed from the water trap. Distillation was continued for a total of three hours, during which time 260 ml (90% of theoretical) methanol-water were removed. During this time, a brown precipitate, which was the crude product, continued to form. After the methanol-water removal, approximately half (2750 ml) of the remaining xylene was removed by distillation.

The reaction mixture was cooled to 30° C. and the crude product was collected by filtration. The filter cake was washed, first with 200 ml of cold xylene, then with about 1500 ml of methanol until the methanol filtrate was clear. The product on air drying weighed 1312 g (76% yield) and melted at 268°-270° C.

The 1312 g of crude 4-acetyl-5,6-bis(p-chlorophenyl)-2H-pyridazin-3-one were placed in a 20 gallon (76.9 liter) glass-lined steel reactor and 47.55 l of ethyl acetate were added. The temperature was raised to reflux (75° C.) and the mixture was stirred until the pyridazin-3-one had completely dissolved. The hot solution was then pressured through a fine cartridge filter to remove insolubles and into a second reactor. Then, 35.61 (75%) of the ethyl acetate were removed by distillation. The slurry in the reactor was cooled to 22° C. and the product was collected on a filter. The filter cake was washed with two 250 ml portions of cold ethyl acetate, and the product was dried to constant weight in a vacuum oven at 90° C. (10 hours). The final weight of purified 4-acetyl-5,6-bis(p-chlorophenyl)-2H-pyridazin-3-one was 1128 g (86% recovery), assaying 99.7% pure.

EXAMPLE 10

4-Acetyl-5,6-bis(p-chlorophenyl)-2H-pyridazin-3-one (3.1 g), ethylene carbonate (2.0 g), and potassium hydroxide (powdered) were dissolved in dimethylformamide (50 ml) and the flask placed in an oil bath (110°-120° C.) until $CO_2$ evolution ceased (ca. 3.5 hours). The reaction mixture was poured into water (400 ml) and chilled at 5° C. for 1 hour. The resulting precipitate was separated by filtration and recrystallized from methanol (85 ml) to afford 4-acetyl-5,6-bis(p-chlorophenyl)-2-(2'-hydroxyethyl)-2H-pyridazin-3-one (68 percent yield) as pale yellow crystals, m.p. 191°-193° C.

Analysis—calculated for $C_{20}H_{16}Cl_2N_2O_3$ (%): C, 59.56; H, 4.00; N, 6.95. Found (%): C, 59.44; H, 3.94; N, 6.71.

While the invention has been described in terms of various preferred embodiments, the skilled artisan will appreciate that various modifications, substitutions, omissions and additions may be made without departing from the spirit thereof. Accordingly, it is intended that the scope of the present invention be limited solely by the scope of the following claims.

What is claimed is:

1. A process for the preparation of a compound of the general formula:

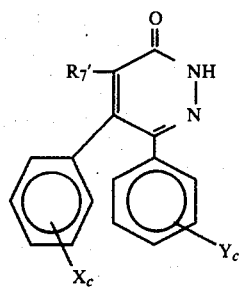

(Ia)

wherein $R'_7$ is acetyl, cyano, phenylsulfonyl, $(C_1-C_4)$alkylhydrazono, naphthyl, phenyl or phenyl substituted with at least one substituent selected from the group consisting of halogen, $C_1-C_6$ alkylamino and $C_1-C_4$ alkoxy; and $X_c$ and $Y_c$ are the same or different and are independently selected from the group consisting of halogen, $C_1-C_4$ alkyl and $C_1-C_4$ alkoxy where c is 0, 1 or 2; which comprises the quinoline catalyzed reaction of a monohydrazone of the formula:

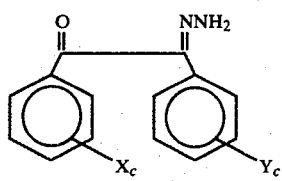

(II)

wherein $X_c$ and $Y_c$ are defined as above, with a substituted acetic acid ester of the formula:

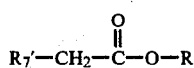

(III)

wherein $R'_7$ is defined as above and R is an alkyl group, in a suitable organic solvent, at elevated temperature.

2. A process according to claim 1 wherein the solvent is xylene.

3. A process according to claim 1 wherein the reaction is carried out at a temperature above 110° C.

4. A process according to claim 1 wherein $X_c$ and $Y_c$ are para-halo.

5. A process according to claim 1 wherein the monohydrazone of formula (II) is p,p'-dichlorobenzil monohydrazone.

6. A process according to claim 1 wherein $R'_7$ is acetyl.

7. A process according to claim 1 wherein R is lower alkyl.

8. A process according to claim 1 wherein the ester of formula (III) is methyl acetoacetate.

9. A process according to claim 1 wherein the ester of formula (III) is ethyl acetoacetate.

10. A process for the preparation of 4-acetyl-5,6-bis(p-chlorophenyl)-2H-pyridazin-3-one which comprises the quinoline catalyzed reaction of p,p'-dichlorobenzil monohydrazone with a lower alkyl acetoacetate, in a suitable organic solvent, at elevated temperature.

11. A process according to claim 10 wherein the solvent is xylene.

12. A process according to claim 10 wherein the reaction is carried out at a temperature above 110° C.

13. A process according to claim 10 wherein the reaction is carried out at reflux temperature.

14. A process according to claim 10 wherein the lower alkyl acetoacetate is methyl acetoacetate.

15. A process according to claim 10 wherein the lower alkyl acetoacetate is ethyl acetoacetate.

16. A process according to claim 11 wherein the lower alkyl acetoacetate is methyl acetoacetate.

17. A process according to claim 11 or 16 wherein the xylene solvent is heated to about 120° C. prior to addition of the reactants and catalyst.

18. A process according to claim 17 wherein the xylene solvent is pre-heated for a period of time sufficient to substantially eliminate any water present in the xylene or in the reaction vessel.

19. A process according to claim 16 wherein the monohydrazone and xylene solvent are combined prior to addition of the methyl acetoacetate and quinoline.

20. A process according to claim 19, wherein the monohydrazone-xylene mixture is heated rapidly to about 125°-130° C. prior to addition of the methyl acetoacetate and quinoline.

21. A process according to claim 20 wherein the methyl acetoacetate and quinoline are added rapidly while maintaining the temperature at about 125°-130° C.

22. A process according to claim 21, wherein after all reactants and catalyst have been added, the reaction mixture is refluxed for about two and one-half to three hours.

23. A process according to claim 16 wherein the methanol-water by-product is removed as it is formed.

24. A process according to claim 16 wherein the product is recrystallized from ethyl acetate.

* * * * *